US009227065B2

(12) United States Patent
Woods et al.

(10) Patent No.: US 9,227,065 B2
(45) Date of Patent: Jan. 5, 2016

(54) METHOD FOR PROGRAMMING IMPLANTABLE DEVICE

(71) Applicant: BOSTON SCIENTIFIC NEUROMODULATION CORPORATION, Valencia, CA (US)

(72) Inventors: Carla M. Woods, Beverly Hills, CA (US); James R. Thacker, Eureka, MO (US); David K. L. Peterson, Saugus, CA (US); Holly A. Segel, Englewood, CO (US); Susan E. Ford, Maumelle, AR (US); Margaret E. Theriot, Willis, TX (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 85 days.

(21) Appl. No.: 14/070,320

(22) Filed: Nov. 1, 2013

(65) Prior Publication Data
US 2014/0058475 A1    Feb. 27, 2014

Related U.S. Application Data

(63) Continuation of application No. 13/538,022, filed on Jun. 29, 2012, and a continuation of application No. 11/105,643, filed on Apr. 13, 2005, now Pat. No. 8,233,991, and a continuation-in-part of application
(Continued)

(51) Int. Cl.
*A61N 1/37* (2006.01)
*A61N 1/36* (2006.01)
(Continued)

(52) U.S. Cl.
CPC ........ *A61N 1/36071* (2013.01); *A61N 1/36185* (2013.01); *A61N 1/37247* (2013.01); *A61N 1/08* (2013.01); *A61N 1/37241* (2013.01)

(58) Field of Classification Search
CPC ........... A61N 1/37241; A61N 1/36185; A61N 1/37247; A61N 1/36071
See application file for complete search history.

(56) References Cited

U.S. PATENT DOCUMENTS 3,646,940 A    3/1972 Timm et al.
3,724,467 A    4/1973 Avery et al.
(Continued)

FOREIGN PATENT DOCUMENTS

EP    0 811 395 A2    10/1997
EP    1 145 736 A2    10/2001
(Continued)

OTHER PUBLICATIONS

PCT International Search Report for PCT/US2011/033070, Applicant: Boston Scientific Neuromodulation Corporation, Form PCT/ISA/210 and 220, dated Jul. 27, 2011 (8 pages).
(Continued)

*Primary Examiner* — Tammie K Heller
(74) *Attorney, Agent, or Firm* — Schwegman Lundberg & Woessner, P.A.

(57) ABSTRACT

A programming system for selecting an electrode configuration for use in a medical electrical stimulator coupled to an electrode array. A programmer is configured for providing a set of electrode configurations for the electrode array, automatically testing a first portion of the set of electrode configurations in a first order, allowing the selection of one or more of the tested electrode configurations, determining whether a suitable number of electrode configurations from among the first portion have been selected within a predefined interval, and automatically testing a second portion of the set of electrode configurations in a second order if the suitable number of electrode configurations from among the first portion are not selected within the predefined interval. The programmer may further allow the selection of the tested electrode configurations, and adjusting parameters during the testing, wherein the adjusting is controllably shared in parallel between a clinician and a patient.

20 Claims, 4 Drawing Sheets

Related U.S. Application Data

No. 11/026,859, filed on Dec. 30, 2004, now Pat. No. 7,881,805, and a continuation-in-part of application No. 10/355,955, filed on Jan. 31, 2003, now Pat. No. 7,146,223.

(60) Provisional application No. 60/354,098, filed on Feb. 4, 2002.

(51) Int. Cl.
*A61N 1/372* (2006.01)
*A61N 1/08* (2006.01)

(56) References Cited

U.S. PATENT DOCUMENTS

| | | |
|---|---|---|
| 3,822,708 A | 7/1974 | Zilber |
| 4,019,518 A | 4/1977 | Maurer |
| 4,505,275 A | 3/1985 | Chen |
| 4,520,825 A | 6/1985 | Thompson et al. |
| 4,793,353 A | 12/1988 | Borkan |
| 5,167,229 A | 12/1992 | Peckham et al. |
| 5,354,320 A | 10/1994 | Schaldach et al. |
| 5,370,672 A | 12/1994 | Fowler et al. |
| 5,417,719 A | 5/1995 | Hull et al. |
| 5,443,486 A | 8/1995 | Hrdlicka et al. |
| 5,501,703 A | 3/1996 | Holsheimer et al. |
| 5,601,617 A | 2/1997 | Loeb et al. |
| 5,626,629 A | 5/1997 | Faltys et al. |
| 5,643,330 A | 7/1997 | Holsheimer et al. |
| 5,649,970 A | 7/1997 | Loeb et al. |
| 5,653,739 A | 8/1997 | Maurer et al. |
| 5,674,264 A | 10/1997 | Carter et al. |
| 5,713,922 A | 2/1998 | King |
| 5,776,171 A | 7/1998 | Peckham et al. |
| 5,776,172 A | 7/1998 | Schulman et al. |
| 5,801,770 A | 9/1998 | Paff et al. |
| 5,814,092 A | 9/1998 | King |
| 5,893,883 A | 4/1999 | Torgerson et al. |
| 5,895,416 A | 4/1999 | Barreras, Sr. et al. |
| 5,913,882 A | 6/1999 | King |
| 5,938,690 A | 8/1999 | Law et al. |
| 6,052,624 A | 4/2000 | Mann |
| 6,058,331 A | 5/2000 | King |
| 6,083,252 A | 7/2000 | King et al. |
| 6,308,102 B1 | 10/2001 | Sieracki et al. |
| 6,381,496 B1 | 4/2002 | Meadows et al. |
| 6,393,325 B1 | 5/2002 | Mann et al. |
| 6,516,227 B1 | 2/2003 | Meadows et al. |
| 6,546,290 B1 | 4/2003 | Shloznikov |
| 6,587,724 B2 | 7/2003 | Mann |
| 6,600,954 B2 | 7/2003 | Cohen et al. |
| 6,609,031 B1 | 8/2003 | Law et al. |
| 6,609,032 B1 | 8/2003 | Woods et al. |
| 6,622,048 B1 | 9/2003 | Mann et al. |
| 6,654,642 B2 | 11/2003 | North et al. |
| 6,709,172 B2 | 3/2004 | Brown |
| 6,792,310 B1 | 9/2004 | Turcott et al. |
| 6,895,280 B2 | 5/2005 | Meadows et al. |
| 6,993,384 B2 | 1/2006 | Bradley et al. |
| 7,146,223 B1 | 12/2006 | King |
| 7,451,473 B2 | 11/2008 | Kawabe et al. |
| 7,519,431 B2 | 4/2009 | Goetz et al. |
| 7,881,805 B2 | 2/2011 | Bradley et al. |
| 7,957,814 B2 | 6/2011 | Goetz et al. |
| 7,974,703 B2 | 7/2011 | Goetz et al. |
| 7,991,482 B2 | 8/2011 | Bradley |
| 8,065,013 B2 | 11/2011 | Bradley et al. |
| 8,233,991 B2 | 7/2012 | Woods et al. |
| 8,931,001 B2 | 1/2015 | Wilson et al. |
| 2001/0034542 A1 | 10/2001 | Mann |
| 2002/0109770 A1 | 8/2002 | Terada |
| 2003/0032992 A1 | 2/2003 | Thacker et al. |
| 2003/0114899 A1 | 6/2003 | Woods et al. |
| 2003/0153959 A1 | 8/2003 | Thacker et al. |
| 2004/0082980 A1 | 4/2004 | Mouine et al. |
| 2004/0117845 A1 | 6/2004 | Karaoguz et al. |
| 2004/0143303 A1 | 7/2004 | Sieracki et al. |
| 2004/0172657 A1 | 9/2004 | Phillips et al. |
| 2004/0215288 A1 | 10/2004 | Lee et al. |
| 2005/0018766 A1 | 1/2005 | Iwamura |
| 2005/0060007 A1 | 3/2005 | Goetz |
| 2005/0060008 A1 | 3/2005 | Goetz |
| 2005/0071883 A1 | 3/2005 | Oh |
| 2005/0203588 A1 | 9/2005 | King |
| 2005/0209655 A1 | 9/2005 | Bradley et al. |
| 2005/0245987 A1 | 11/2005 | Woods et al. |
| 2005/0245992 A1* | 11/2005 | Persen et al. ............ 607/60 |
| 2005/0246757 A1 | 11/2005 | Relan et al. |
| 2005/0267605 A1 | 12/2005 | Lee et al. |
| 2006/0017324 A1 | 1/2006 | Pace et al. |
| 2006/0171453 A1 | 8/2006 | Rohlfing et al. |
| 2006/0294565 A1 | 12/2006 | Walter |
| 2007/0083896 A1 | 4/2007 | Staples |
| 2007/0180482 A1 | 8/2007 | Frink et al. |
| 2007/0199032 A1 | 8/2007 | Renkis |
| 2008/0071325 A1 | 3/2008 | Bradley |
| 2009/0118787 A1 | 5/2009 | Moffitt et al. |
| 2010/0010566 A1 | 1/2010 | Thacker et al. |
| 2013/0006325 A1 | 1/2013 | Woods et al. |

FOREIGN PATENT DOCUMENTS

| | | |
|---|---|---|
| EP | 2 039 391 A1 | 3/2009 |
| WO | WO 01/43818 A1 | 6/2001 |
| WO | WO 2004/041351 A1 | 5/2004 |
| WO | WO-2004041351 A1 | 5/2004 |
| WO | WO 2006/112852 A2 | 10/2006 |

OTHER PUBLICATIONS

PCT Written Opinion of the International Searching Authority for PCT/US2011/033070, Applicant: Boston Scientific Neuromodulation Corporation, Form PCT/ISA/237, dated Jul. 27, 2011 (7 pages).
Office Action dated Feb. 6, 2013 in U.S. Appl. No. 13/090,073, filed Apr. 19, 2011, (16 pages).
Amendment filed Apr. 30, 2013 in U.S. Appl. No. 13/090,073, filed Apr. 19, 2011, (10 pages).
Final Office Action dated Aug. 19, 2013 in U.S. Appl. No. 13/090,073, filed Apr. 19, 2011, (17 pages).
PCT International Preliminary Report on Patentability (Chapter I of the Patent Cooperation Treaty) for PCT/US2011/033070, Applicant: Boston Scientific Neuromodulation Corporation, FOrm PCT/IB/326 and 373, dated Nov. 1, 2012 (9 pages).
U.S. Appl. No. 13/538,022, filed Jun. 29, 2012, Method For Programming Implantable Device.
U.S. Appl. No. 11/031,648, filed Jan. 7, 2005, Method For Optimizing Location of Implanted Electrode Array During Implant Surgery.

* cited by examiner

METHOD FOR PROGRAMMING IMPLANTABLE DEVICE

RELATED APPLICATION DATA

This application is a continuation of U.S. application Ser. No. 13/538,022, which is a continuation of U.S. application Ser. No. 11/105,643, filed on Apr. 13, 2005, now issued as U.S. Pat. No. 8,233,991, which is a continuation-in-part application of, and claims the benefit of priority to U.S. application Ser. No. 11/026,859, filed on Dec. 30, 2004, now issued as U.S. Pat. No. 7,881,805, which is a continuation-in-part application of U.S. application Ser. No. 10/355,955, filed on Jan. 31, 2003, now issued as U.S. Pat. No. 7,146,223, which claims the benefit of and priority to U.S. Provisional Application Ser. No. 60/354,098, filed on Feb. 4, 2002. These prior applications are incorporated herein by reference in their entirety

BACKGROUND OF THE INVENTION

The present invention relates to medical electrical stimulators, such as Spinal Cord Stimulation (SCS) systems and more particularly to methods for efficiently selecting electrode configurations. An SCS system, used herein as an example of a medical electrical stimulator of the invention, treats chronic pain by providing electrical stimulation pulses through the individual contacts (a.k.a., electrodes) of an electrode array (a.k.a., a lead) placed epidurally next to a patient's spinal cord. The combination of stimulation pulses delivered to the electrodes of an electrode array constitutes an electrode configuration. In other words, an electrode configuration represents each polarity, being positive, negative, or zero of each of the electrodes. Other parameters that may be controlled or varied in SCS and other forms of medical electrical stimulation are the frequency of pulses provided through the electrode array, pulse width, and the strength (amplitude) of pulses delivered. Amplitude maybe measured in milliamps, volts, etc. In some SCS systems, the "distribution" of the current/voltage across the electrodes may be varied such that the polarity of each electrode is not a whole number value, but represents a fraction of positive or negative values. Moreover, there may be some electrodes that remain inactive for certain electrode configurations, meaning that no current/voltage is applied through the inactive electrode(s). Therefore, for such systems, each electrode configuration also represents a polarity percentage of each active electrode of an electrode array.

Previous SCS technology identified these parameters and effectuated stimulation through an electrode array or lead at specific electrode configurations. However, previous SCS technologies attempted to evaluate parameters, including electrode configuration, strength, pulse width, etc., one at a time. An optimized stimulation parameter set for a specific patient may be determined from the response of the patient to various sets of stimulation parameters. There is, however, an extremely large number of possible combinations of stimulation parameters, and evaluating all possible sets is very time consuming, and perhaps impractical.

Spinal cord stimulation is a well accepted clinical method for reducing pain in certain populations of patients. An SCS system typically includes an Implantable Pulse Generator (IPG), electrodes, electrode lead, and, if needed, one or more electrode lead extensions. Some systems, rather than using an IPG, include an implanted Radio-Frequency receiver that receives pulses from an external transmitter. In either case, the electrodes are implanted along the dura of the spinal cord, and the IPG generates electrical pulses that are delivered, through the electrodes, to the dorsal column and dorsal root fibers within the spinal cord. Individual electrode contacts (the "electrodes") are arranged in a desired pattern and spacing in order to create an electrode array. Individual wires within one or more electrode leads connect with each electrode in the array. The electrode leads exit the spinal column and generally attach to one or more electrode lead extensions or, depending on the length of the leads, they may attach directly to the IPG. The leads and/or lead extensions are typically tunneled around the torso of the patient to a subcutaneous pocket where the IPG is implanted.

Spinal cord stimulators and other stimulation systems are known in the art. For example, an implantable electronic stimulator is disclosed in U.S. Pat. No. 3,646,940 issued Mar. 7, 1972 for "Implantable Electronic Stimulator Electrode and Method" that provides timed sequenced electrical impulses to a plurality of electrodes. As another example, U.S. Pat. No. 3,724,467 issued Apr. 3, 1973 for "Electrode Implant For The Neuro-Stimulation of the Spinal Cord," teaches an electrode implant for the neuro-stimulation of the spinal cord. A relatively thin and flexible strip of physiologically inert plastic is provided as a carrier on which a plurality of electrodes are formed. The electrodes are connected by leads to an RF receiver, which is also implanted.

In U.S. Pat. No. 3,822,708, issued Jul. 9, 1974 for "Electrical Spinal Cord Stimulating Device and Method for Management of Pain," another type of electrical spinal cord stimulation device is taught. The device disclosed in the '708 patent has five aligned electrodes, which are positioned longitudinally on the spinal cord. Electrical pulses applied to the electrodes block perceived intractable pain, while allowing passage of other sensations. A patient-operated switch allows the patient to adjust the stimulation parameters.

Electrode arrays currently used with known SCS systems may employ between one and sixteen electrodes on a lead or leads. Electrodes are selectively programmed to act as anodes, cathodes, or left off, creating an electrode configuration. The number of electrode configurations available, combined with the ability of integrated circuits to generate a variety of complex stimulation pulses, presents a huge selection of stimulation parameter sets to the clinician. When an SCS system is implanted, a "fitting" procedure is performed to select an effective stimulation parameter set for a particular patient. Such a session of applying various stimulation parameters and electrode configurations may be referred to as a "fitting" or "programming" session. Additionally, a series of electrode configurations to be applied to a patient may be organized in a steering table or in another suitable manner.

A known practice is to manually test one parameter set, and then select a new stimulation parameter set to test, and compare the results. Each parameter set is painstakingly configured and increased in amplitude gradually to avoid patient discomfort. A clinician often bases his selection of a new stimulation parameter set on his/her personal experience and intuition. There is no systematic method to guide the clinician. If the selected stimulation parameters are not an improvement, the clinician repeats these steps, using a new stimulation parameter set, based only on dead-reckoning. The combination of the time required to test each parameter set, and the number of parameter sets tested, may result in a very time consuming process. For instance, a system with 16 selectable electrodes contains over 40 million possible combinations of electrode configurations alone. Thus, testing all possible combinations is impractical.

In order to achieve an effective result from spinal cord stimulation, the lead or leads may be placed in a location such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy.

In order to test the effectiveness on a particular patient of various stimulation parameters and electrode configurations, it is necessary to provide a series of stimulation parameters in a systematic method. Several such systems exist including the systems disclosed in U.S. Pat. No. 6,393,325, herein incorporated by reference in its entirety, wherein a patient may direct the movement of the stimulus current through a suitable interface.

Another method of testing the effectiveness of various stimulation parameters is disclosed in U.S. application Ser. No. 11/026,859, herein incorporated by reference in its entirety. In this Application, during a fitting session with a patient, a clinician uses navigation with two parameter tables to step through and optimize stimulation parameters.

The inventors have ascertained that improved methods are needed for selection of electrode configurations during navigation through a programming session, whereby each patient may efficiently optimize and personalize his/her stimulation treatment in terms of stimulation strength, pulse rate, pulse width, and electrode configuration.

SUMMARY OF THE INVENTION

The present invention addresses the above and other needs by providing methods for selecting stimulation electrode configurations, which methods guide users toward effective stimulation treatments. In one embodiment of the invention, a method for selecting electrode configurations for use in a medical electrical stimulator is provided. The method may comprise: (1) providing a set of electrode configurations for at least the active electrodes of an electrode array; (2) automatically testing at least a first portion of the set of electrode configurations in a first order; (3) allowing the selection of one or more of the tested electrode configurations; and (4) automatically testing at least a second portion of the set of electrode configurations in a second order if a suitable number of electrode configurations from among said first portion are not selected within a predefined interval.

The rate at which the electrode configurations are tested may be controlled. For example, the rate at which the configurations are tested may correspond to about a 5% change in current amplitude per second to about a 50% change in current amplitude per second. Selection of the electrode configurations may be by a patient or may be by objective criteria. Methods may further comprise the steps of re-testing the selected electrode configurations for fine-tuning. The selected electrode configurations may be stored and organized.

The electrode configurations may correspond to stimulation of a particular part or section of a patient's body. For example, a user may select a particular area of the body by virtue of an interface device. The electrode configurations may then be applied to the patient, as the patient (or attending clinician) is allowed to select particular electrode configurations that are effective. A programming tool may be used to group together related series of electrode configurations. Therefore, the starting electrode configuration may correspond to a stimulation directed to a particular part or section of a patient's body. The starting electrode configuration may be selected by a program or by a user or it may correspond to a particular portion of the electrode array corresponding to a particular part of the patient's body or section of the area of potential stimulation.

The methods may also comprise clinician, automatic or patient control of other stimulation parameters as the electrode configurations are being applied to the patient. For example, a user may adjust one or more stimulation parameters before or during the testing. These stimulation parameters include polarity or polarity percentage, amplitude, pulse width, pulse rate, and combinations thereof. Various levels of shared control of the other stimulation parameters may be distributed between an automated system, a clinician, and the patient.

The methods may further comprise: (1) interrupting the continuous testing, (2) selecting a second starting electrode configuration, (3) continuously testing the set of electrode configurations in an order based on the second starting electrode configuration, and (4) allowing the selection of one or more of the tested electrode configurations.

Another embodiment is a method for selecting an electrode configuration for use in a medical electrical stimulator, comprising: (1) providing a set of electrode configurations the active electrodes of an electrode array; (2) automatically testing at least a portion of the set of electrode configurations; (3) allowing the selection of one or more of the tested electrode configurations; (4) adjusting one or more parameters during the testing, wherein the parameters are selected from the group consisting of polarity, polarity percentage, amplitude, pulse width, pulse rate, and combinations thereof, and wherein the adjusting is controllably shared between a clinician and a patient.

Another embodiment of the present invention is a method for selecting an electrode configuration for use in a medical electrical stimulator, comprising: (1) providing a set of electrode configurations for at least each active electrode of an electrode array; and (2) testing an effective number of electrode configurations of the set of electrode configurations by, wherein the testing comprises: (a) sweeping through each section of an area of potential stimulation provided by one or more implanted electrode arrays; (b) marking electrode configurations that are effective; (c) testing electrode configurations near any marked electrode configurations; and (d) allowing the selection of one or more of the tested electrode configurations. The sweep may be completed in less than about five minutes.

In another embodiment, an electrode selection system is provided. A system may comprise (1) a neural stimulation system, the neural stimulation system having a multiplicity of implantable electrodes, (2) an implantable pulse generator connected to the implantable electrodes, (3) electrical circuitry means within the implantable pulse generator for applying a prescribed current stimulus through a selected electrode configuration of the implantable electrodes, (4) a device coupled to the implantable pulse generator for storing and delivering a set of electrode configurations to the pulse generator, (5) means for applying the set of electrode configurations to a patient, and (6) means for allowing user selection of one or more of the electrode configurations in the series.

The system may further comprise means for generating and displaying a sequence of instructional displays that guide a user through the process of selecting one or more electrode configurations. The system may also comprise means for displaying a graphical representation of a human body such that the set of electrode configurations being applied to the patient is correlated to a part of the human body and such correlation is indicated on the graphical representation. The system may also comprise means for displaying a generic graphic that represents a relative two-dimensional map such that the set of electrode configurations being applied to the patient is correlated to the relative two-dimensional position of the stimulation area and such correlation is indicated on the graphical representation.

Another embodiment of the invention is an electrode selection system comprising: (1) a neural stimulation system, the neural stimulation system having a multiplicity of implantable electrodes, (2) an implantable pulse generator connected to the implantable electrodes, (3) electrical circuitry means within the implantable pulse generator for applying a prescribed current stimulus through a selected electrode configuration of the implantable electrodes, (4) a memory device coupled to the implantable pulse generator for storing a set of electrode configurations, wherein each electrode configuration represents a polarity or a polarity percentage of each active electrode of an electrode array, wherein the implantable pulse generator automatically tests at least a portion of the set of electrode configurations in order based on a starting electrode configuration, and (5) a user interface device for allowing the selection of one or more of the tested electrode configurations.

It is thus a feature of the present invention to provide a method for determining optimum electrode configurations without requiring exhaustive testing associated with creating, optimizing and testing each parameter of each electrode configuration. A set of electrode configurations is applied to a patient for selection by the patient. By providing a systematic method for searching for effective electrode configurations, a therapeutic session may be specifically developed for each patient Once one or more electrode configurations are selected and identified by a patient or clinician, these selected electrode configurations may be optimized. An electrode configuration may be adjusted for amplitude (stimulation strength), pulse width, and pulse rate. One such an optimizing procedure is described more fully in U.S. application Ser. No. 11/026,859.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

Appendix A, known as a steering table, herein incorporated by reference, is an example of a set of electrode configurations.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The methods of the present invention provide systematic approaches for selecting stimulation parameter sets, or electrode configurations, for medical electrical stimulators. A Spinal Cord Stimulation (SCS) system will be used herein as an example of such a medical electrical stimulator. The methods lead a user through a selection process that efficiently locates optimum electrode configurations. The selection process and system may also herein be referred to as "fitting," "programming," "navigating" a "fitting system," or a "fitting program." Thus, a user is allowed to navigate through the millions of electrode configurations to determine a customized treatment. As used herein, the term "user" may refer to a patient, a clinician, an automated program, or a combination thereof.

Figures 1, 2:
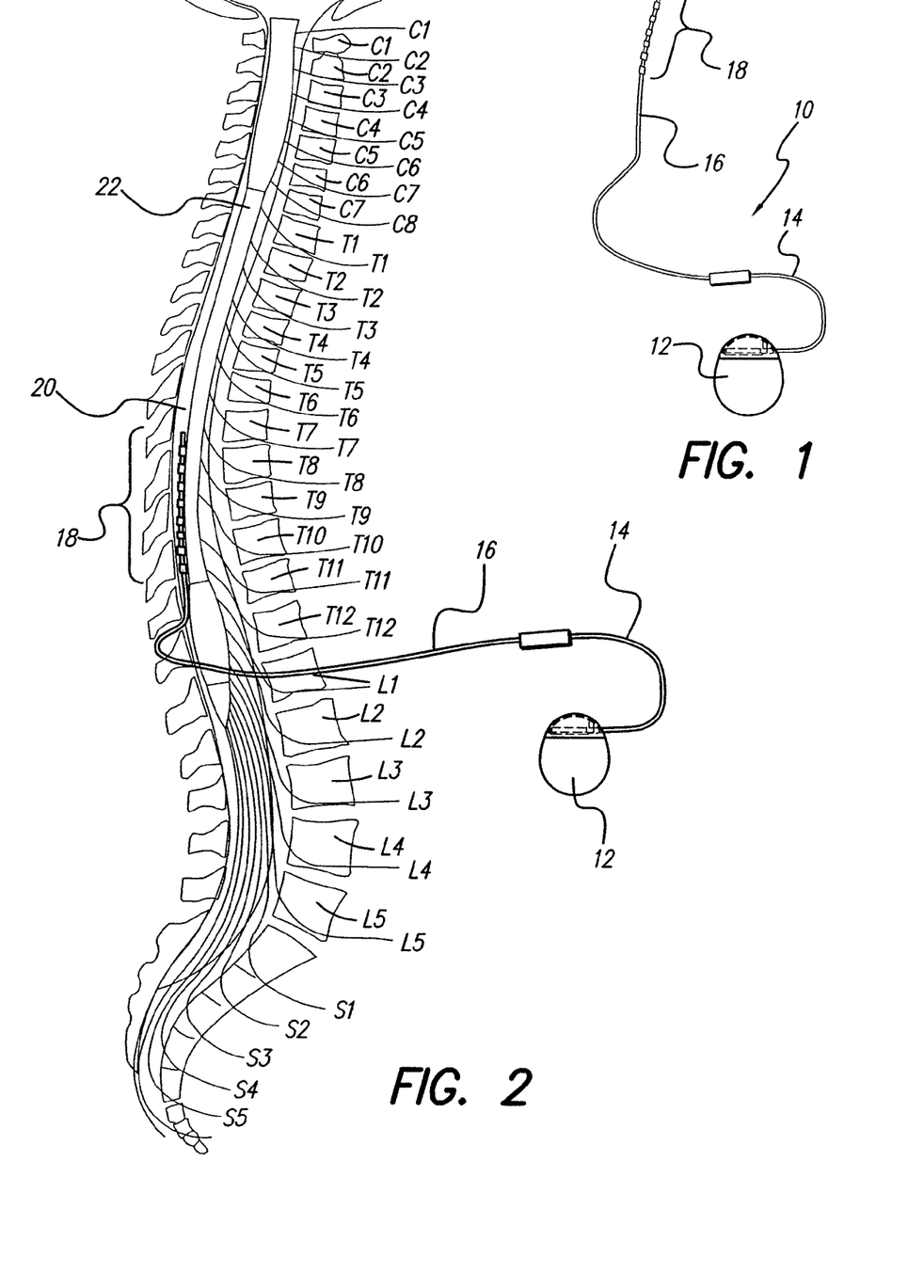
FIG. 1 shows a Spinal Cord Stimulation (SCS) system, as an example of a medical electrical stimulator.
FIG. 2 depicts the SCS system of FIG. 1 implanted in a spinal column.

An exemplary Spinal Cord Stimulation (SCS) system 10 is shown in FIG. 1. SCS system 10 comprises an Implantable Pulse Generator (IPG) 12, an optional lead extension 14, an electrode lead 16, and an electrode array 18. The IPG 12 generates stimulation current for implanted electrodes that make up the electrode array 18. When needed, a proximal end of the lead extension 14 is removably connected to the IPG 12 and a distal end of the lead extension 14 is removably connected to a proximal end of the electrode lead 16. Alternatively, a proximal end of lead 16 is attached directly to the IPG 12. Electrode array 18 is formed on a distal end of the electrode lead 16. The in-series combination of the lead extension 14 and electrode lead 16, carry the stimulation current from the IPG 12 to the electrode array 18.

The SCS system 10 described in FIG. 1 above is depicted implanted in the epidural space 20 in FIG. 2. The electrode array 18 is implanted at the site of nerve fibers that are the target of stimulation, e.g., along the spinal cord. Due to the lack of space near the location where the electrode lead 16 exits the spinal column, the IPG 12 is generally implanted in the abdomen or above the buttocks. When needed, the lead extension 14 facilitates locating the IPG 12 away from the electrode lead exit point.

In a preferred embodiment, one, two or more electrode arrays 18 may be implanted in the patient. Having a relatively greater number of electrodes increases the area of the body that can be affected by stimulation, or the "area of potential stimulation." The area of potential stimulation corresponds roughly to the area of the body mapped to the dermatomes for the area of the spine adjacent to the implanted electrodes. The area of potential stimulation may be divided into sections, each section corresponding to the electrodes that typically provide stimulation to that section of the body.

A more detailed description of a representative SCS system that may be used with the present invention is described in U.S. Pat. No. 6,516,227, incorporated herein by reference in its entirety. It is to be emphasized, however, that the invention herein described may be used with many different types of stimulation systems, and is not limited to use only with the representative SCS system described in the U.S. Pat. No. 6,516,227 Patent.

The systems and methods explained herein provide a programming or navigation system used to select electrode configurations useful for providing stimulation to a patient. Automated systems and methods offer an alternative to manual selection and testing of electrode configurations to find an appropriate stimulation therapy, e.g., for pain management. Manual selection of electrode configurations has proven to be time consuming and complicated. Electrodes may be manually selected to be positive, negative, or turned off, such that a subset of anodes and cathodes are selected from a total set to create a stimulation delivery electrode configuration. One problem with manual selection, as discussed in the background section, is that it is sometimes a trial and error process, requiring a sophisticated understanding of current field generation. The present systems and methods provide for an easy-to-use navigational system, which allows for patient control, while testing a maximum number of electrode configurations. The present systems and methods eliminate the need to manually select electrode polarity. The present systems and methods eliminate the need to train clinicians on the complications of current field generation. Instead, a large number of electrode configurations is consecutively applied to a patient for testing.

Figure 3:
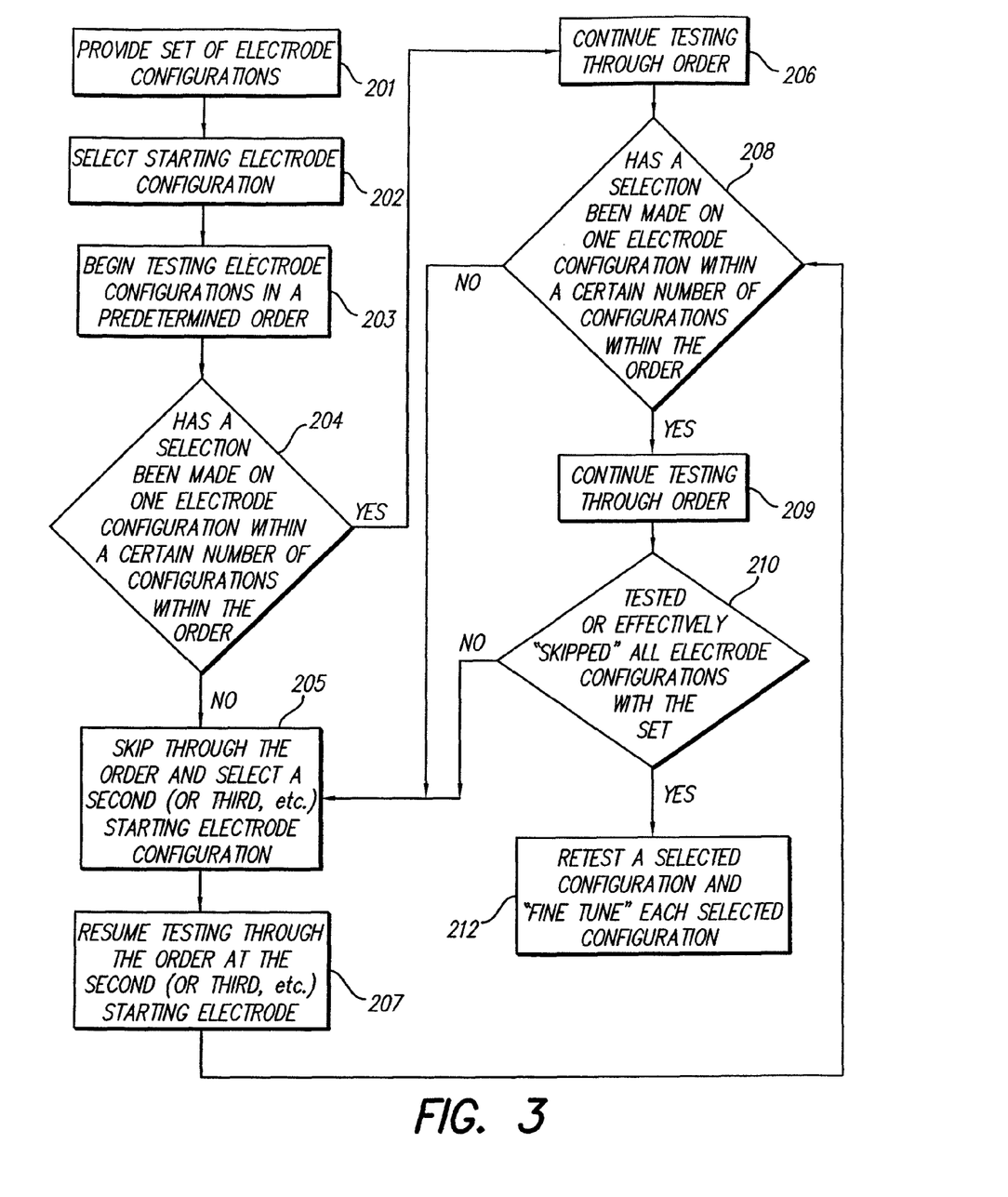
FIG. 3 depicts a flow chart according to one embodiment of the present invention.

A flow chart representing one embodiment of a method for electrode configuration testing is depicted in FIG. 3. As with most flow charts, each step or act of the method is represented in a "box" or "block" of the flow chart. Each box or block, in turn, has a reference number associated with it to help explain the process in the description that follows.

A set of electrode configurations is provided at step 201, such as the set illustrated in Appendix A. The exemplary electrode configurations may be arranged in a predetermined order, as shown in Appendix A, may be determined by parameters in software, may be established by an algorithm, may be decided by combinations thereof, or equivalents. A table such as shown in Appendix A may be referred to as a steering table. A steering table typically comprises rows, with each row defining each electrode configuration. In a preferred embodiment, each row specifies the polarity or polarity percentage on each electrode of each electrode array 18 (FIGS. 1 and 2). Each electrode array 18 preferably comprises four or eight electrodes, but certain embodiments may only utilize a subset or superset of the electrode array 18, for example three or twelve electrodes, respectively. In a preferred embodiment, one or two electrode arrays, each having eight electrodes, are used, resulting in a steering table having eight or sixteen entries per row, respectively (the latter is shown in the example of Appendix A), or nine or seventeen entries per row, respectively (one for each electrode and one for the case of the stimulator, which may also function as an electrode). Those skilled in the art will recognize that a steering table may include, in addition to polarity definitions, other parameters, such as pulse duration and/or pulse frequency, and that table with such other variations is intended to come within the scope of the present invention.

When polarity percentages are used, rather than just simple polarity settings, the polarity distribution of the rows of the steering table may differ by about 0.05 in value, such as the one illustrated in Appendix A, or by any other suitable order of magnitude. The polarity associated with the electrodes in the electrode array, or a subset or superset of the electrode array, may be summed to zero. For example, one electrode of the electrode array may have a polarity of negative one (cathode), while another electrode may have a polarity of positive one (anode), such as the entry corresponding to Entry No. 21 of Appendix A. Entry No. 21 defines Electrode No. 1 as a cathode and Electrode No. 3 as an anode.

The rows in the steering table may be ordered or arranged based on the physical characteristics of the stimulation provided by each electrode configuration, so that moving from one row to the next in the steering table represents a gradual, and somewhat uniform, change in stimulation. In other words, stepping from one row to an adjacent row in the steering table causes the stimulation applied to the tissue through the individual electrodes of the electrode array 18 to gradually move in a desired direction. This type of current steering is described more fully in U.S. Pat. No. 6,393,325, which is incorporated herein by reference in its entirety.

Once the desired set of electrode configurations or steering table has been provided, a starting electrode configuration is selected (step 202). For example, the first row of the steering table may be tested first, followed in order by the remaining rows. The rows may be ordered, as explained above, by current steering methods. Groups of electrode configurations (groups of rows within a steering table) may correspond to a certain part of a patient's body. For example, electrodes No. 1 through No. 3 may correspond to stimulating the lower right leg of a patient when programmed in a particular configuration. However, the order of rows is not essential to these embodiments, and the rows may be arranged in any order. The starting electrode configuration may also be selected as corresponding to a particular section of the area of potential stimulation created by one or more implanted electrode arrays. The steering table may be arranged by portions of the electrode array corresponding to the sections, as well. For example, in Appendix A, Entries Nos. 21-41 correspond to electrodes No. 1-4, or a first portion of the electrode array, corresponding to a first section of the area of potential stimulation.

A clinician or patient may select a row as the starting electrode configuration. This selection may be based on an area of the body to be stimulated by the SCS system. Alternatively, the starting electrode may be predetermined, determined by a program or algorithm, through a user interface, or randomly. A patient may choose from a few possibilities of starting electrode configurations. For example, the patient may choose from a discrete number of trial electrode configurations to select the starting configuration. Such a selection from a discrete number of trial configurations is explained more fully in U.S. patent application Ser. No. 11/026,859.

Once the starting electrode configuration is selected, stimulation is applied to the patient, as a program automatically steps through each entry or row of the steering table from the selected starting electrode configuration. For example as seen in Appendix A, if Entry No. 21 is the starting electrode configuration, this stimulation is applied to the patient, followed by the stimulation represented in Entry Nos. 22, 23, etc. As each electrode configuration is consecutively tested on the patient, the patient or attending clinician has the power to select, highlight or mark any particular electrode configuration of the set being tested. For example, a patient may select a particular configuration that feels good, or specifically targets an area of the body. The patient may provide this feedback as to the effectiveness of the stimulation that has been applied as represented by the electrode configuration entries of the steering table.

Objective criteria may also be used to select from the electrode configurations being tested. Alternative means (e.g., objective measurements of various physiological parameters of the patient, such as perspiration, muscle tension, respiration rate, heart rate, and the like) may also be used to judge the effectiveness of the applied stimulation. Selected electrode configurations may be stored for further testing.

The change in polarity or polarity distribution for consecutive electrode configurations tested may be varied during stimulation or predetermined, such as by selection of an appropriate steering table. For example, the entries for one or more electrodes in two consecutive rows in the steering table of Appendix A may differ by about 5% in polarity distribution. An automated program may test electrode configurations at a more drastic change in polarity distribution, such as up to 50% distribution change on one or more electrodes, per electrode configuration tested. The automated program could skip to every tenth row of a table such as the table of Appendix A, or a different steering table could be used, with rows that differ in polarity distribution for one or more electrodes by 0.50 per row. Such change in the polarity distribution may be limited by a patient's discomfort with the distribution changes during row transitions. A more gradual change in the polarity distribution may result in a more comfortable application of the stimulation to the patient. However, changes in the polarity distribution should be large enough so as to effectively test enough electrode configurations in a given clinical time period. A polarity distribution change of about 1% may not be "fast" enough to test a suitable number of electrode configurations during the fitting session.

To avoid uncomfortable over-stimulation, the stimulation amplitude may be initially set to a relatively low level, perhaps even below the level that will result in the patient perceiving paresthesia. The stimulation level at which the patient begins to perceive paresthesia is called the perception or perceptual threshold. See e.g., U.S. Pat. No. 6,393,325, noted above. The stimulation may be increased until it begins to become uncomfortable for the patient. This level is called the maximum or discomfort threshold. See e.g., U.S. Pat. No. 6,393,325, noted above. These pre-navigation measured thresholds may be noted before the selection of the starting electrode configuration. Alternatively, these thresholds may be determined based on pre-established values, or based on previously-measured thresholds for the patient.

Additionally, the amplitude may be adjusted by the user during the testing of the electrode configurations. In other words, while the automated program steps through the entries of the steering table, a user may pay attention to the strength of the stimulation being applied. The electrode configurations represent the polarity or the polarity percentage of the individual electrodes of the array. The steering table entries denote polarity using a positive or negative "1" or, for polarity percentage or polarity distribution, a fraction thereof. The total current applied through each electrode may be about 1 to about 13 milliamps, up to a "grand total" of 20 milliamps applied through all active electrodes combined. The values of the electrode configurations therefore represent a percentage of this grand total current applied. Alternatively, the stimulation amplitude may be quantified by voltage applied to the electrodes. A user may vary this strength of stimulation while the automated program circulates through the configuration of polarities as seen in the steering table.

Therefore, the amplitude or stimulation strength may be adjusted by a patient, clinician or program before or during a testing session. The pulse width and or frequency may also be controlled or adjusted before or during the testing of the electrode configurations.

The electrode configurations may be tested in any order, such as the order of the rows in the steering table (step 203). In order to efficiently move through all the electrode configurations of the set, a pace may be set or adjusted. A suitable rate or pace may be a current shifting rate of about 5% per 1-3 seconds to about 50% per second. A suitable pause in between rows, entries or electrode configurations may be about 0.1 to about 5 seconds. This time allows a patient, clinician, or program to select the tested electrode configuration. Preferably, about 0.2 to about 10 electrode configurations may be tested per second. More preferably, about 1 electrode configuration per 1-3 seconds should be applied to a patient to allow for adequate testing and possible selection of such electrode configuration.

In order to rapidly move through the steering table and test an effective number of the electrode configurations on the patient, a navigation program may be used. A navigation program may allow a user to "skip" through part of the steering table if a relatively low number of entries are being selected in that particular part of the table. For example, if no selections have been made within about 20 successive rows of a steering table, the program may move ahead a certain number of entries to another point within the steering table. Successive row testing may then resume at this point in the steering table. The point where the testing resumes may also be referred to as a second (or third, etc.) starting electrode configuration if such skipping is accomplished. Interrupting the sequence of the steering table to move ahead may be prompted by any objective criteria. Additionally, a user may be allowed to skip ahead to test another area of the body. Referring to step 204 of FIG. 3, if no selections have been made within a certain number of configurations (rows or entries), a program allows the user to skip to another section of the steering table (step 205). Alternatively, another steering table may be provided having a second order of electrode configurations to be tested. When and how to skip entries is related to known characteristics of the electrode configurations arranged in the steering table, as explained above. If a patient is making selections frequently enough, the program continues to test the electrode configurations in the order as defined by the rows of the steering table (step 206).

As seen in step 207, testing is resumed through the steering table at the second (or third, etc.) starting electrode configuration. Once testing is resumed, the patient still has an option to select one or more of the configurations. If the user continues not to select electrode configurations frequently enough, the program is prompted again (step 208) to forward to another section in the steering table for testing. In this continuous manner (step 209), each electrode configuration may be tested or effectively skipped by a user (step 210).

The selected electrode configurations may be further tested on the patient for "fine tuning" (step 212). Such fine tuning may be done in the manner described by U.S. application Ser. No. 11/026,859, wherein it is described that once an electrode configuration is selected from one table, a more detailed table may be used to test entries "before" and "after" the selected entry. For example, if an electrode configuration was selected from a steering table that varied from row to row by 0.05 in relative current (milliamps), a more detailed table may vary from row to row by 0.01 current. As explained in U.S. application Ser. No. 11/026,859, if entry No. 1 of the steering table is selected by a user (or program) during the navigation, this entry may correspond to an entry of the more detailed table, e.g., Entry No. 1001 of a more detailed table (not shown). Thus, Entry No. 1001 thus serves as a "benchmark."

Once a benchmark is identified in the more detailed table, entries above and below the benchmark are tested for fine tuning. For example, going "down" in the more detailed table, Entry No. 1002 is applied, then No. 1003, and then No. 1004, and so on, until the patient (or other means) determines that no further improvement results, at least going in that direction in the more detailed table. For example, Entry No. 1002 may be found to be the most effective electrode configuration in that direction in the more detailed table.

In a similar manner, going "up" in the more detailed table from the benchmark (No. 1001), means that Entry No. 1000 is applied, then No. 999, then No. 998, and so on, until the patient (or other means) determines that no further improvement results in that direction in that portion of the table. For example, Entry No. 998 may be found to be the most effective electrode configuration in that direction and that section of the more detailed table.

Once at least two Stimulation Sets, e.g., No. 998 and 1002, have been identified, then a determination may be made as to which one is the most effective to use for stimulation. The sets chosen to be the most effective, e.g., Stimulation Set No. 998, is selected as the best one to use for stimulation in this instance, and the re-testing for the original selected Entry No. 1 from the steering table is completed. Other fine-tuning methods or re-testing may be employed. Fine-tuning and/or re-testing may be done for all the selected electrode configurations of the steering table. Such selections may be saved for this patient such that fitting does not have to reoccur prior to each treatment session. The selections may also be used in other aspects of the system.

Furthermore, the methods discussed above are not limited to use with a steering table. Any method in which stimulation is transitioned along the electrode array may be used. For example, stimulation may be defined by parameters specified by software. As another example, stimulation may be activated in one portion of an array and an algorithm may be used to transition stimulation from that portion of the electrode array to another or from one end of the array to the other without the use of a steering table. Fixed step sizes may be used to transition stimulation, or a method such as the method disclosed in U.S. application Ser. No. 11/026,859, may be used to determine the appropriate step sizes to use for ordering the set of electrode configurations.

In order to rapidly and efficiently move through a fitting session to test an effective number of the electrode configurations on the patient, other parameter controls may be implemented. For example, a suitable time for a fitting session may be determined for a patient, such as, for example, between about 15 to about 60 minutes. A suitable number of configurations should be tested during the fitting session. The number of electrode configurations that are tested during the fitting depends on the patient as well as the therapeutic goals for the fitting. Based on the optimal time of the session and therapeutic goals of the sessions, parameters may be controlled to test this effective number of electrode configurations during the fitting session. For example, the rate of applying successive electrode configurations may be controlled, adjusted, increased, or decreased to effectively move through all of the electrode configurations to be tested. Additionally, the change in the polarity distribution of the electrode configurations being applied may be controlled. In controlling these parameters, effective fitting in the allotted therapy time may be accomplished.

Other methods may be used to help ensure that a relatively larger number of different electrode configurations are tested in an efficient manner. For example, software (or other means, such as the patient or clinician) controlling a fitting session may be programmed to start with an electrode configuration corresponding to a first section of the area of potential stimulation. The stimulation may then be transitioned (or "swept") through some electrode configurations for that section and then through some electrode configurations for other sections, in a relatively short period of time, e.g., five minutes. During this first "sweep" through each section, the patient may select or mark electrode configurations and/or stimulation parameter sets that appear to be effective. The software might then optionally sweep through the sections again, using different electrode configurations and/or stimulation parameter sets than were used in the first sweep. Again, the patient may select or mark electrode configurations and/or stimulation parameter sets that appear to be effective. Once one or more sweeps is completed, the software can then return to electrode configurations that the patient marked and "sweep" through various configurations near the marked configurations in order to locate the locally optimal electrode configuration. The "fine tuning" methods described above and in U.S. application Ser. No. 11/026,859 may also be used to test configurations near the marked configurations. The patient or clinician can then select the optimal electrode configuration(s) from the locally optimal configurations. If a suitable number of configurations are not marked within a sweep through a section (which number may be, for example, two, five, ten, or determined by the system, the clinician, the patient, or a combination thereof), the system may skip to the next section. Thus, the method of this example enables the testing of electrode configurations from different portions of the electrode array(s) as well as localized testing of electrode configurations near configurations identified by the patient as effective in an efficient and effective manner.

Various levels of patient control may be used before and during a fitting session, such as navigation. Control may be shared between the clinician and the patient. Patients may use a handheld device or other suitable interface that allows her to control the navigation and the adjustment of parameters between identified bounds. There may be a program that allows the clinician to select the level of patient control. Because no two patients are alike, the degree of patient control may be assessed for each patient. Thus, a system that allows the clinician to select the degree, level or amount of patient control would be more time efficient and allow for individualized fitting sessions. A clinician may select this level of control before or during a fitting session. Additionally, a clinician may use information from previous stimulation sessions with such patient to determine stimulation control. Allowing an appropriate level of patient control reduces patient anxiety over the fitting session and also enhances the effectiveness of patient/clinician communication.

In fitting sessions, control may be parallel between the clinician and the patient. However, based upon the patient's level of control, the patient may be given priority of control over a clinician, effectively allowing the patient control to override the clinician control. Such priority to the patient's selection, decisions, and control may be given only to specific parameters. For example, the patient may be given priority control for the adjustment of amplitude, pulse width, and/or pulse rate. The clinician, however, may have the priority in deciding how to steer navigation through the navigational fitting session.

Other combinations of patient, clinician and automated control are possible. For example, electrode configuration variations (e.g., via movement through a steering table) may be fully automated and thus blocked from patient control, while a patient is free to adjust amplitude. A patient may also have both amplitude and current field steering control. Most likely, all patients should have priority control to lower or reduce the applied amplitude of any stimulation. Thus, the patient controlled amplitude down "button" would have priority over either clinician or automated controls. These programmable control variations allow for flexibility in safe fitting sessions. Better patient outcomes are received due to reduced communication difficulties.

Figure 4:
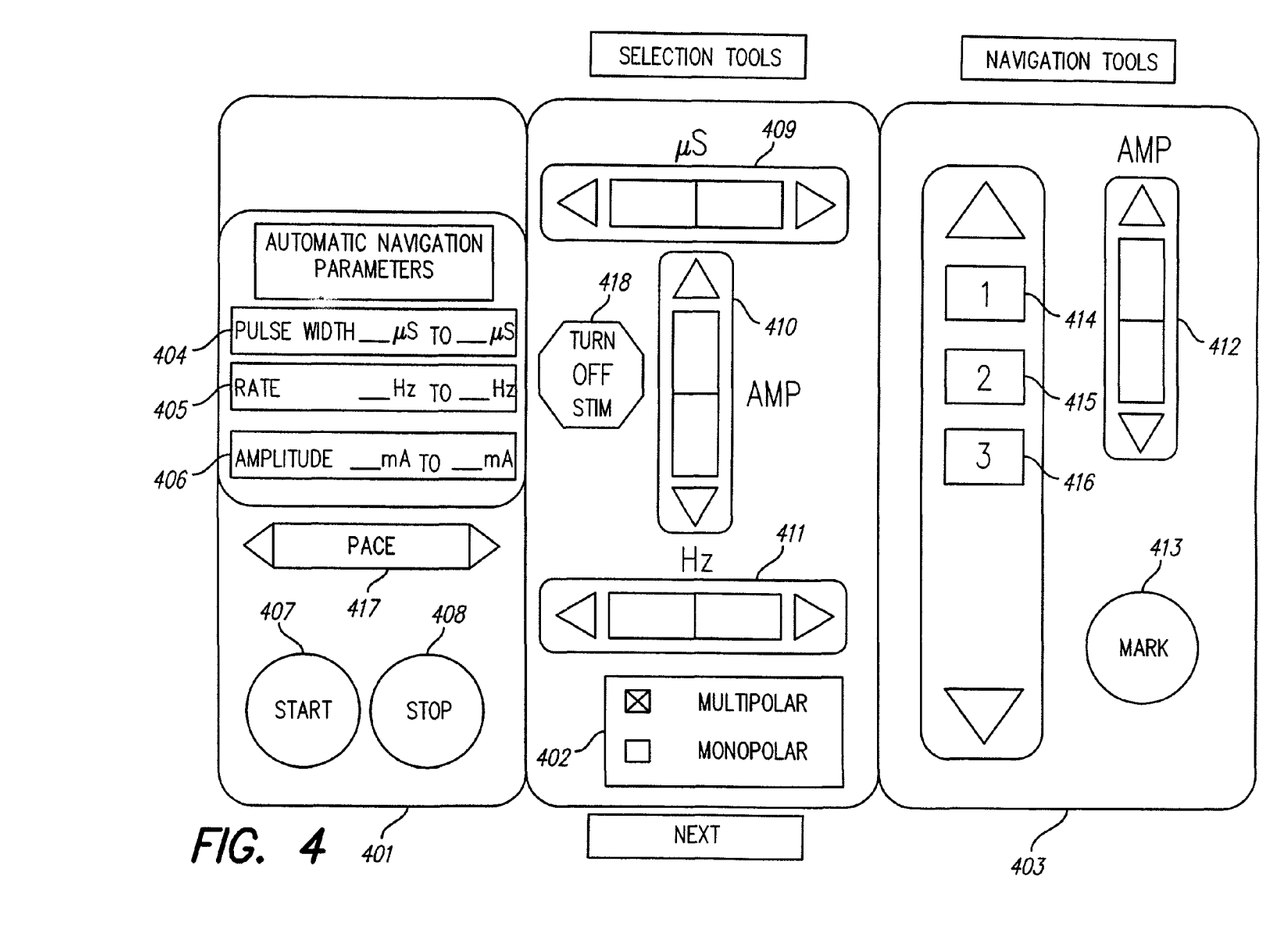
FIG. 4 depicts a user interface that may be used during navigation through the electrode configurations.

Any suitable user interface may be incorporated into embodiments of the invention. For example, the interfaces described in U.S. Pat. No. 6,393,325 may be used or altered for the navigational fitting system described herein. Additionally, the interface displayed in FIG. 4 may be used to guide a user through the fitting program. As seen in FIG. 4, the interface may include three panels, or any combination or portion of the three panels (401, 402, 403). In the 401 panel, automatic navigation parameters may be set such as pulse width 404, rate 405 and amplitude or strength 406. The interface may also have a start 407 and stop 408 switch that halts or resumes the automated navigation, respectively. The user may be able to adjust the pulse width 409, amplitude 410 or rate 411, as well as entirely halt delivery of stimulation pulses, i.e., turn simulation off 418, within the interface displayed at panel 402. In panel 403, a user may be able to adjust the amplitude 412. The user is also able to highlight, mark, or select 413 the electrode configurations being tested. The user may be able to select from 414, 415, and 416, which correspond to sets of electrode configurations to be tested. Finally, the pace 417 may be varied during the navigation so as to adjust the speed at which consecutive electrode configurations are applied. As described above, a suitable pace may be about 1 electrode configuration per 1-3 seconds. Each parameter may be adjusted by the user within the bounds determined by the clinician and/or automated system.

Although the interface controls of FIG. 4 are illustrated as being a touch screen, any other interface device that allows adjustment of these various parameters may be designed. For example, a hand-held user control device may be used having these parameter controls. Also, although the controls of FIG. 4 may appear to be "buttons" any other suitable controls may be used, such as sliding scales or dials.

Figure 5:
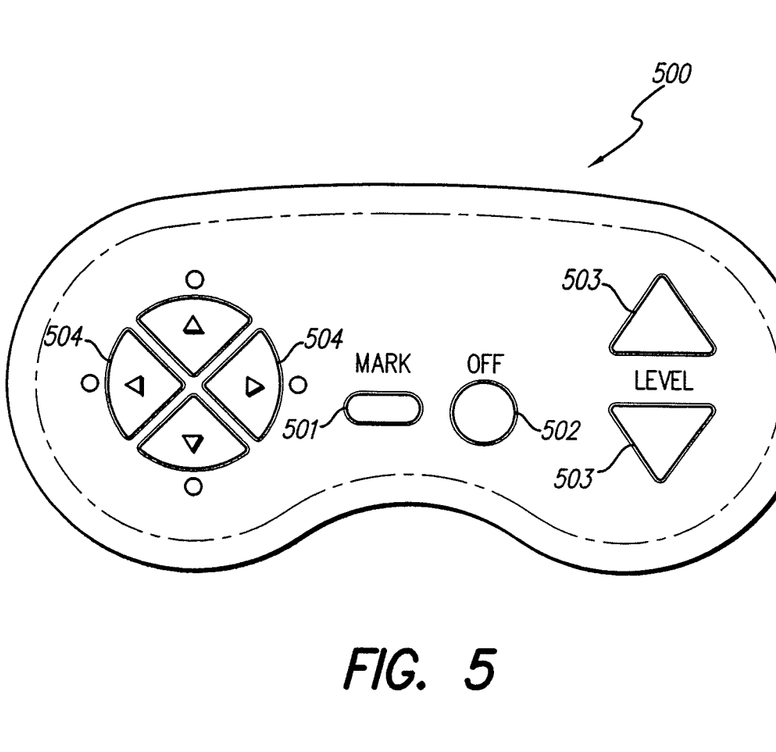
FIG. 5 depicts a user interface device that may be used during navigation through the electrode configurations.

One such suitable hand-held device for allowing user adjustment of the stimulation parameters is depicted in FIG. 5. The hand-held device 500 may be small and easy to manipulate. The patient is given control to mark, highlight or select 501 electrode configurations. Additionally, the patient may turn the navigation session "off" 502 with a suitable safety or escape button. The patient may adjust the amplitude 503 through a pair of increase and decrease buttons. Finally, with a series of four directional buttons 504, the patient may be able to gradually shift paresthesia locations on the body until pain coverage is obtained.

Clinician and patient control may be shared as explained above. In one embodiment, the clinician uses the interface described in FIG. 4, while the patient uses the hand-held device depicted in FIG. 5. Thus, during navigation, the clinician has the ability to control all of the parameters, while the patient may have a simplified hand-held device that allows for control of only a few parameters. The selection of a suitable hand-held device may depend of patient sophistication. In other words, a patient may "graduate" from a simplified device to a more advanced device, allowing her greater control over the navigation session.

The methods of the present invention may be incorporated into any medical electrical stimulator, such as any SCS, neural or muscle stimulation system. Thus, in another embodiment, a stimulation system is provided. A system may comprise: (1) a neural stimulation system, the neural stimulation system having a multiplicity of implantable electrodes, (2) an implantable pulse generator connected to the implantable electrodes, (3) electrical circuitry means within the implantable pulse generator for applying a prescribed current stimulus through a selected electrode configuration of the implantable electrodes, (4) a device coupled to the implantable pulse generator for storing and delivering a set of electrode configurations to the pulse generator, (5) means for applying the set of electrode configurations to a patient in one or more series, and (6) means for allowing user selection of one or more of the electrode configurations in the series.

Another embodiment of the invention is an electrode selection system comprising: (1) a neural stimulation system, the neural stimulation system having a multiplicity of implantable electrodes, (2) an implantable pulse generator connected to the implantable electrodes, (3) electrical circuitry means within the implantable pulse generator for applying a prescribed current stimulus through a selected electrode configuration of the implantable electrodes, (4) a memory device coupled to the implantable pulse generator for storing a set of electrode configurations, wherein each electrode configuration represents a polarity or polarity percentage of each active electrode of an electrode array, wherein the implantable pulse generator automatically tests at least a portion of the set of electrode configurations based on a starting electrode configuration, and (5) a user interface device for allowing the selection of one or more of the tested electrode configurations. Such stimulation systems and devices involved in such systems are more fully described in U.S. Pat. No. 6,393,325 and related applications and issued patents.

While the invention herein disclosed has been described by means of specific embodiments and applications thereof, numerous modifications and variations could be made thereto by those skilled in the art without departing from the scope of the invention set forth in the claims. For example, the methods discussed above are not limited to spinal cord stimulation systems and may be used with many kinds of stimulation systems such as, but not limited to, cochlear implants, cardiac stimulation systems, peripheral nerve stimulation systems, brain stimulation systems and microstimulators.

What is claimed is:

1. A stimulation system, comprising:
an implantable stimulator configured for delivering electrical current to a spinal cord tissue in accordance with different electrode configurations; and
a user interface device, configured for, in response to a user actuation of a first control, instructing the implantable stimulator to incrementally transition the delivered electrical current through the different electrode configurations, and in response to a user actuation of a second control, instructing the implantable stimulator to adjust the speed at which the electrode configurations are applied.

2. The stimulation system of claim 1, wherein the user interface device is configured for, in response to the user actuation of the first control, instructing the implantable stimulator to incrementally transition the delivered electrical current through the different electrode configurations in a manner that causes stimulation of tissue to gradually move in a defined direction.

3. The stimulation system of claim 1, wherein the user interface device is further configured for programming at least one of the electrode configurations into the implantable stimulator.

4. The stimulation system of claim 1, wherein the user interface device is a touchscreen.

5. The stimulation system of claim 1, wherein the user interface device is a hand-held device.

6. The stimulation system of claim 1, wherein the implantable stimulator is an implantable pulse generator (IPG).

7. The stimulation system of claim 1, wherein the defined speed is one electrode configuration per 1-3 seconds.

8. The system of claim 1, wherein the system is configured to limit a change in adjusted speed to a change in current amplitude per second.

9. The system of claim 1, wherein the user interface device is configured to receive a user-selection of an electrode configuration being tested, the system further comprising a steering table with a plurality of entries corresponding to the different electrode configurations, the system being configured to skip entries in the steering table if a low number of entries is selected.

10. The system of claim 1, wherein:
the system further comprises a steering table with a plurality of entries corresponding to the different electrode configurations;

instructing the implantable stimulator to incrementally transition the delivered electrical current through the different electrode configurations includes instructing the implantable stimulator to transition to different entries within the plurality of entries to test about 0.2 to about 10 electrode configurations per second.

11. The system of claim 10, wherein the user interface device is configured to adjust at least one stimulation parameter.

12. The system of claim 1, wherein incrementally transitioning the delivered electrical current includes implementing a program to automatically transition the delivered electrical current through different electrode configurations.

13. The system of claim 1, wherein the user interface is configured to receive an input to select a starting electrode configuration.

14. A method of providing therapy to a patient, comprising:
delivering electrical current to a tissue region in accordance with different electrode configurations;
incrementally transitioning the delivered electrical current through the different electrode configurations at a defined speed of one electrode configuration per 1-3 seconds in response to a user actuation of a first control mechanism; and
adjusting the defined speed in response to a user actuation of a second control mechanism.

15. The method of claim 14, the delivered electrical current is incrementally delivered through the different electrode configurations in a manner that causes stimulation of the tissue region to gradually move in a defined direction.

16. The method of claim 14, further comprising programming at least one of the electrode configurations into an implantable stimulator.

17. The method of claim 14, wherein the tissue region comprises spinal cord tissue.

18. A method of providing therapy to a patient, comprising:
delivering electrical current to spinal cord tissue in accordance with different electrode configurations;
incrementally transitioning the delivered electrical current through the different electrode configurations at a defined speed in response to a user actuation of a first control mechanism; and
adjusting the defined speed in response to a user actuation of a second control mechanism.

19. The method of claim 18, the delivered electrical current is incrementally delivered through the different electrode configurations in a manner that causes stimulation of the tissue region to gradually move in a defined direction.

20. The method of claim 18, further comprising programming at least one of the electrode configurations into an implantable stimulator.

* * * * *